(12) United States Patent
von Schuckmann

(10) Patent No.: US 6,401,712 B1
(45) Date of Patent: Jun. 11, 2002

(54) INHALER

(75) Inventor: Alfred von Schuckmann, Kevelaer (DE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 09/171,761

(22) PCT Filed: Apr. 25, 1997

(86) PCT No.: PCT/EP97/02144

§ 371 (c)(1),
(2), (4) Date: May 11, 1999

(87) PCT Pub. No.: WO97/40876

PCT Pub. Date: Nov. 6, 1997

(30) Foreign Application Priority Data

| Apr. 25, 1996 | (DE) | ......... 196 16 418 |
| May 2, 1996 | (DE) | ......... 196 17 555 |
| May 15, 1996 | (DE) | ......... 196 19 536 |

(51) Int. Cl.⁷ ............................................. A61M 15/00
(52) U.S. Cl. ........................... 128/203.15; 128/203.12
(58) Field of Search ................ 128/200.11, 200.12, 128/203.12, 203.15, 203.19, 203.21; 239/202.27, 102.1, 102.2

(56) References Cited

U.S. PATENT DOCUMENTS

| 2,549,303 A | | 4/1951 | Friden | |
| 4,064,878 A | | 12/1977 | Lundquist | |
| 5,042,472 A | * | 8/1991 | Bunin | 128/203.15 |
| 5,181,189 A | | 1/1993 | Hafner | |
| 5,192,548 A | * | 3/1993 | Velasquez et al. | 128/203.12 |
| 5,207,217 A | * | 5/1993 | Cocozza et al. | 128/203.15 |
| 5,229,164 A | | 7/1993 | Pins | |
| 5,239,991 A | * | 8/1993 | Chawla et al. | 128/203.15 |
| 5,415,162 A | * | 5/1995 | Casper et al. | 128/203.12 |
| 5,457,895 A | | 10/1995 | Thompson | |
| 5,622,166 A | * | 4/1997 | Eisele et al. | 128/203.12 |
| 5,642,727 A | * | 7/1997 | Datta et al. | 128/203.15 |
| 5,669,973 A | * | 9/1997 | Pletcher | 128/203.15 |
| 5,673,685 A | * | 10/1997 | Heide et al. | 128/203.15 |
| 5,785,049 A | * | 7/1998 | Smith et al. | 128/203.15 |

FOREIGN PATENT DOCUMENTS

| EP | 0129985 | 1/1985 |
| EP | 0189276 | 7/1986 |
| EP | 0393942 | 10/1990 |
| EP | 0511726 | 11/1992 |
| EP | 0525720 | 2/1993 |
| WO | 9609085 | 3/1996 |

* cited by examiner

Primary Examiner—John G. Weiss
Assistant Examiner—Teena Mitchell
(74) Attorney, Agent, or Firm—Martin A. Farber

(57) ABSTRACT

An inhaler having an inhaler body extending between two ends, an outlet at one of said two ends, a succion tube at the other of said two ends and an inhalation channel within the body providing fluid connection between the suction tube and the outlet, the suction tube being shaped and dimensioned for insertion into a blister containing powder such that the drawing of air through the inhaler body will draw powder from the blister through the suction tube and inhalation channel and out of the outlet, a channel inlet being provided in the suction tube and a cutter being provided around only part of the channel inlet to cut a fin cover of a blister around only part of the channel inlet, at least one inlet passage extending between a passage inlet at a position along the length of the suction tube and a passage outlet adjacent the channel inlet to allow air into a blister and blister packs which are distinguishable according to their orientation and/or contents.

53 Claims, 13 Drawing Sheets

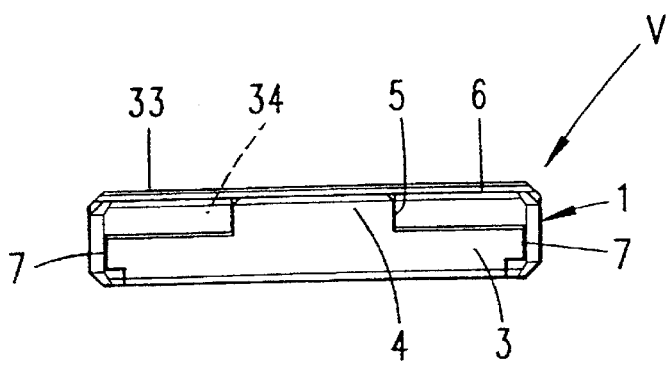
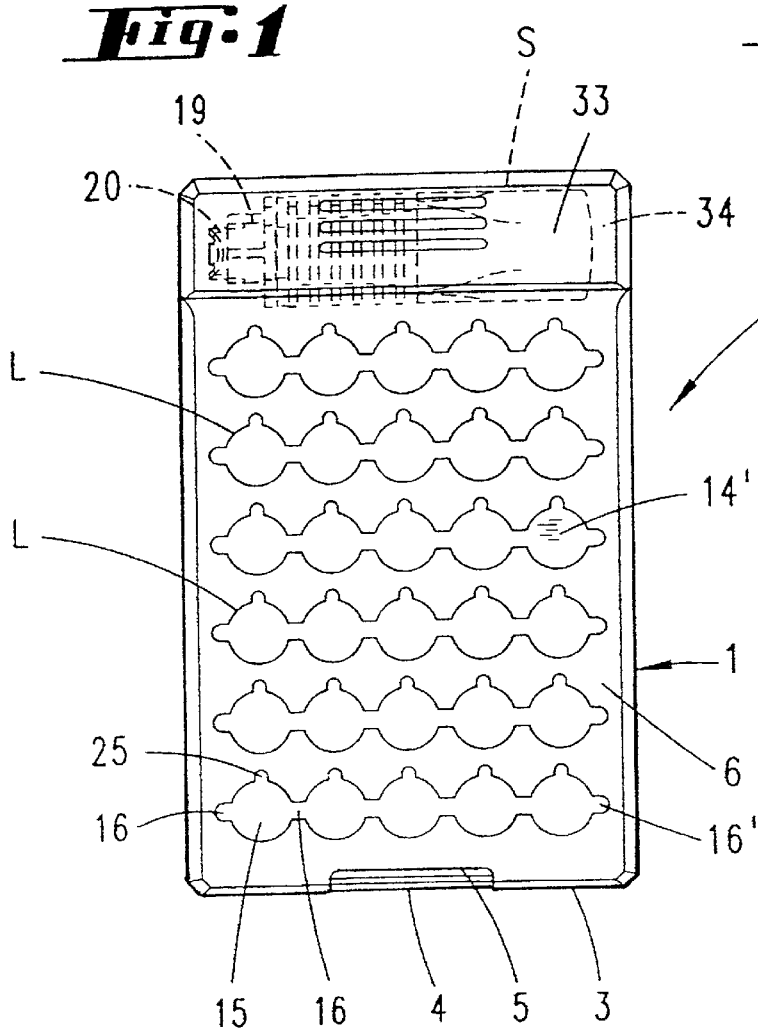
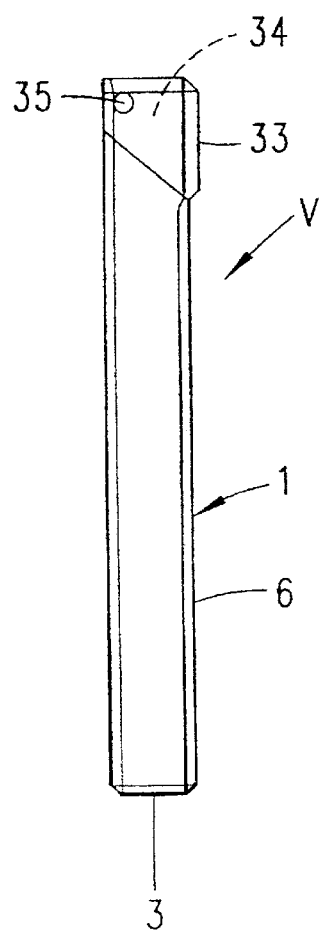

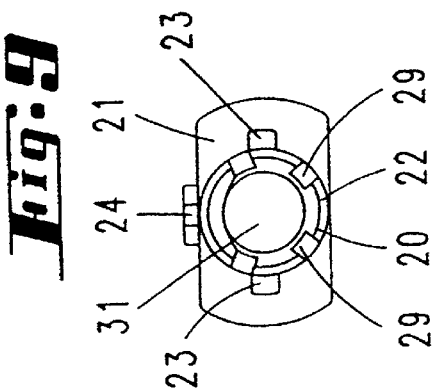
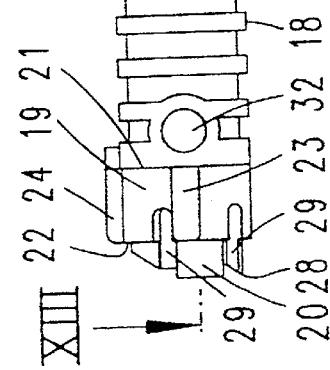
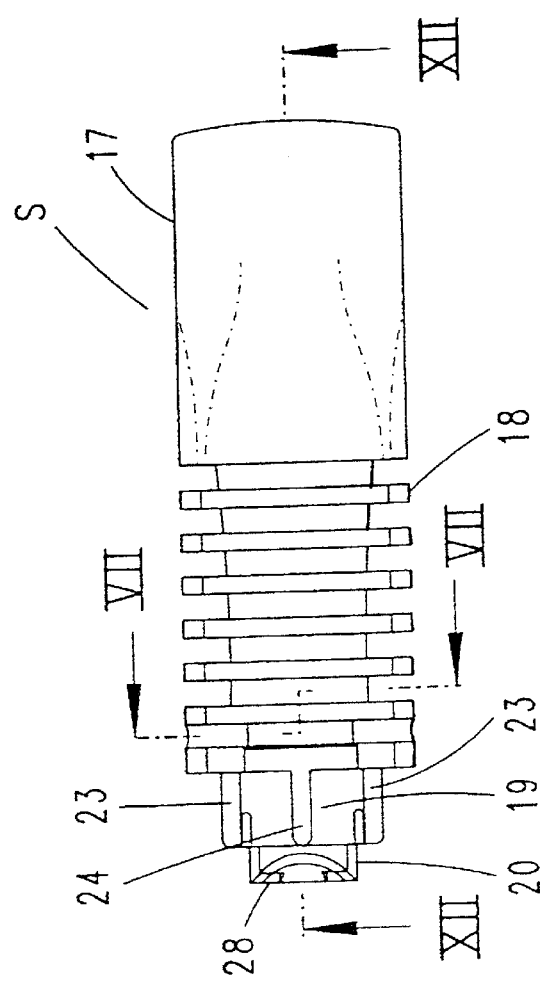
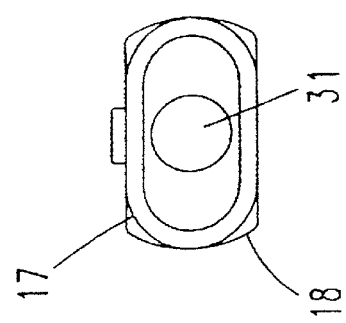
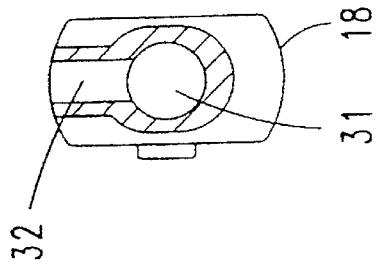

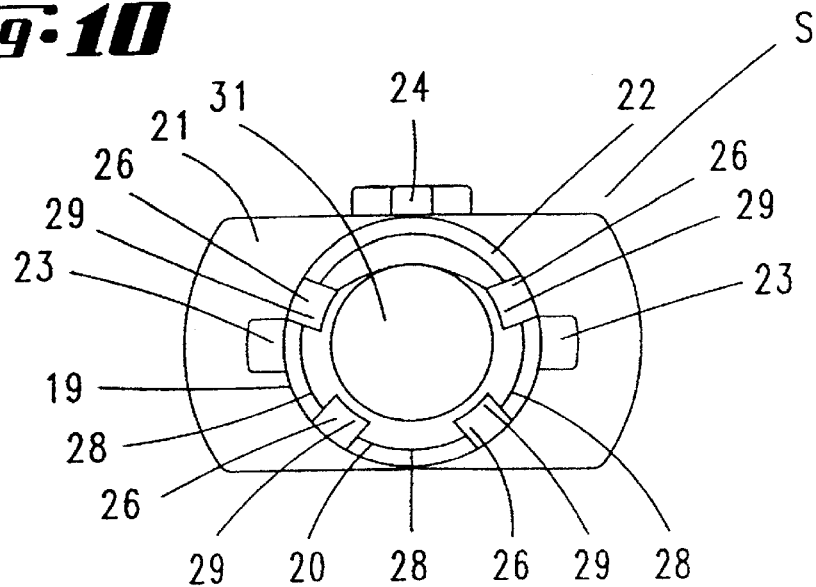
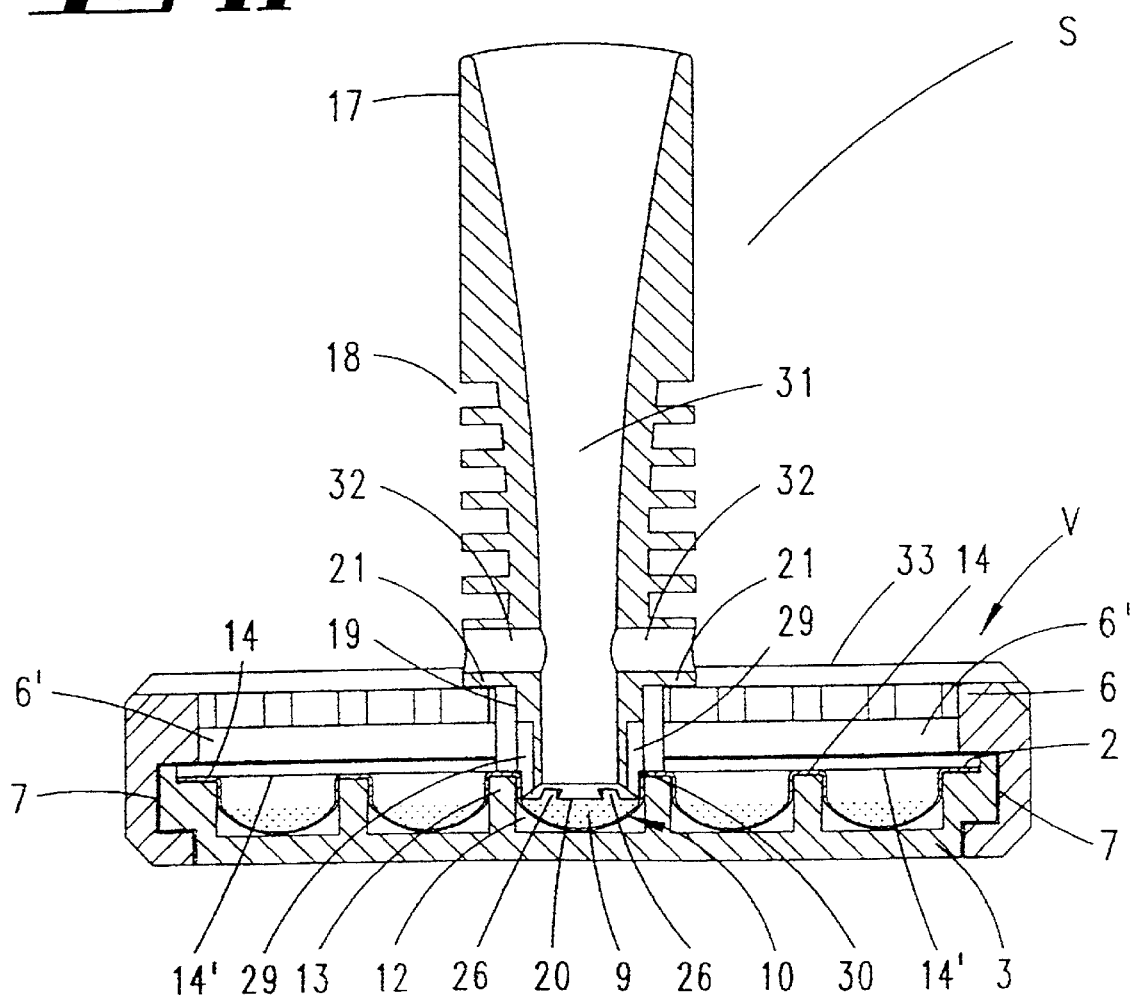

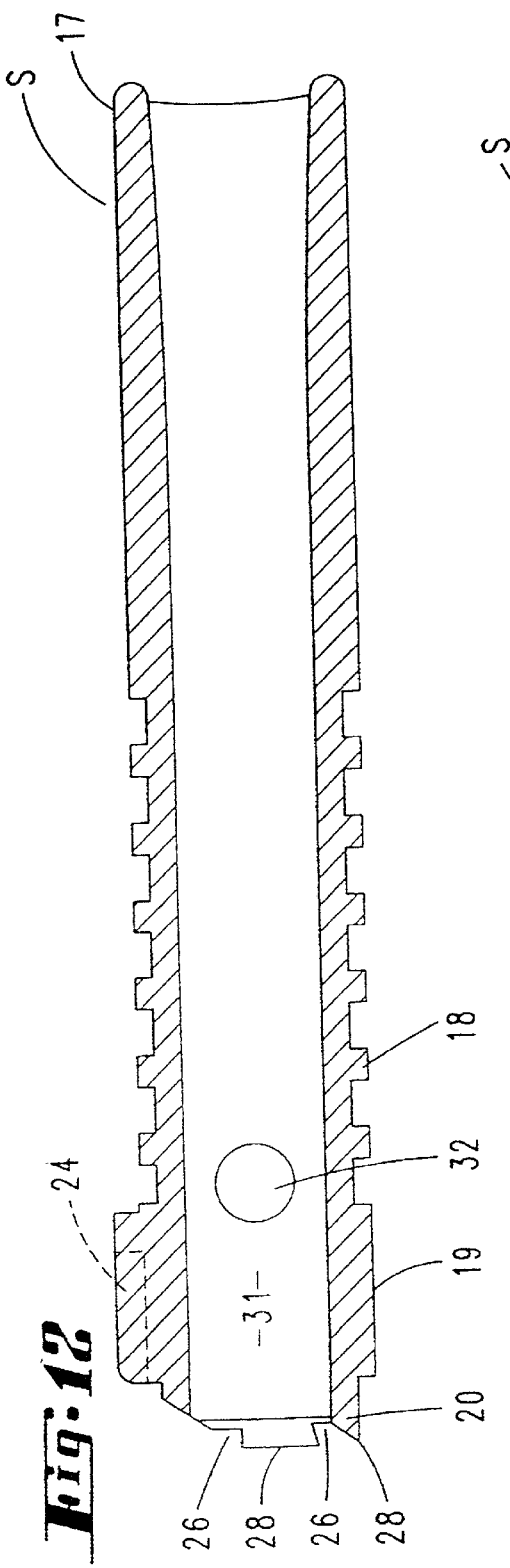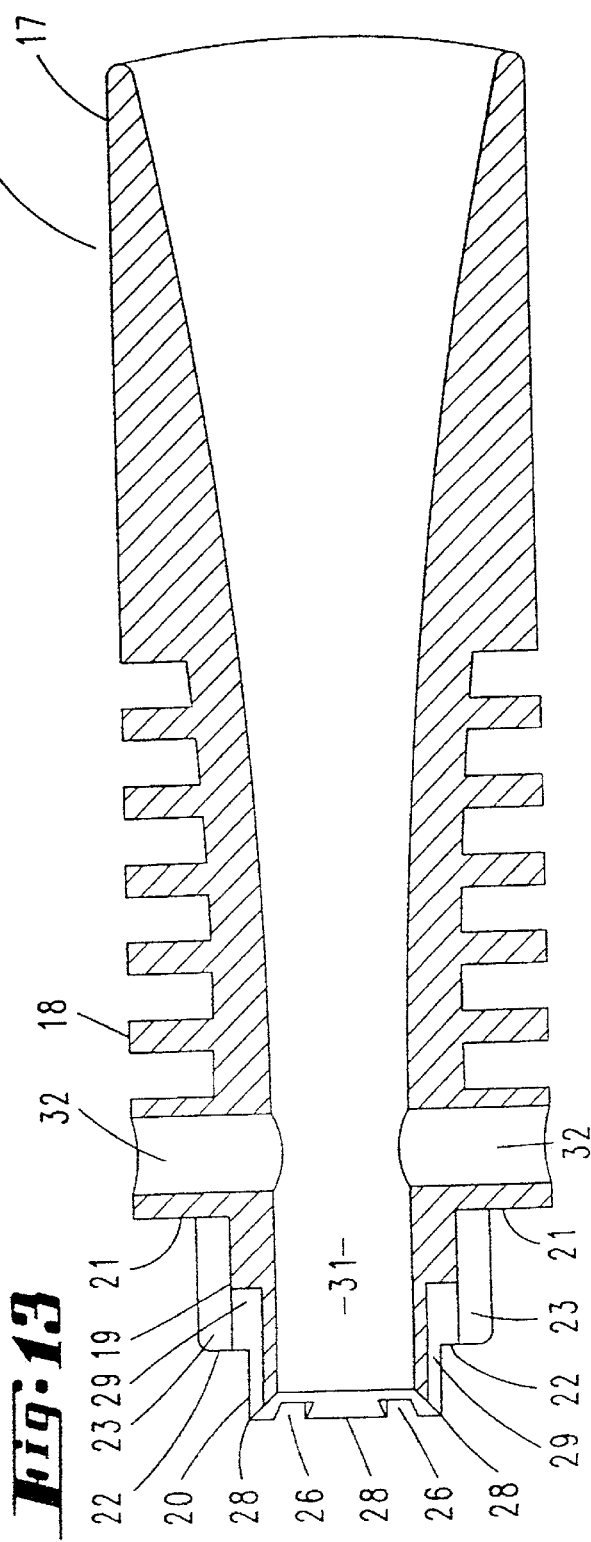

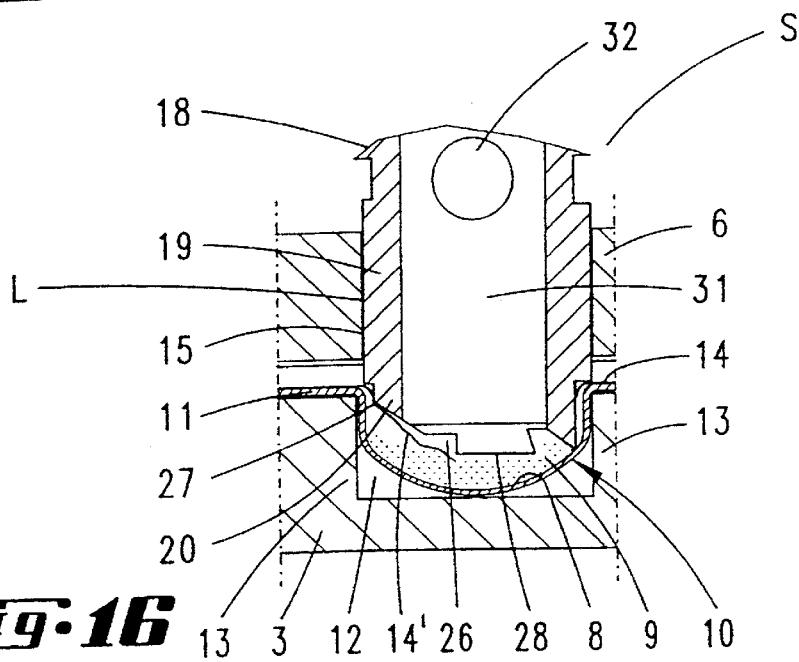
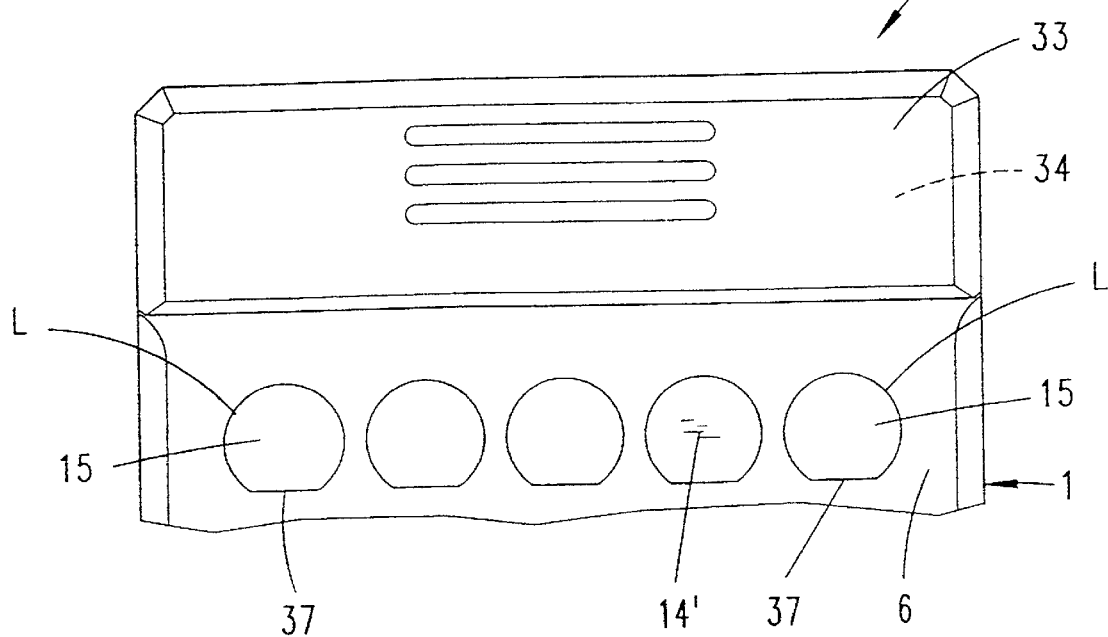

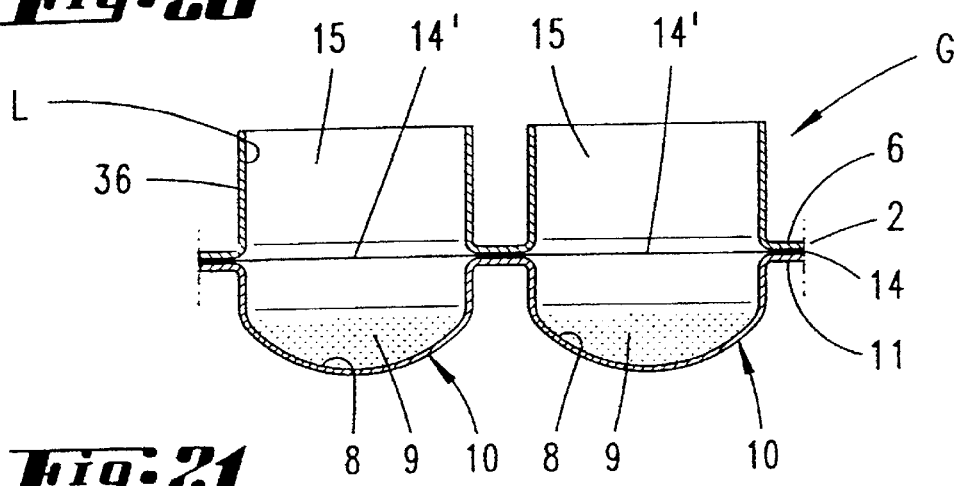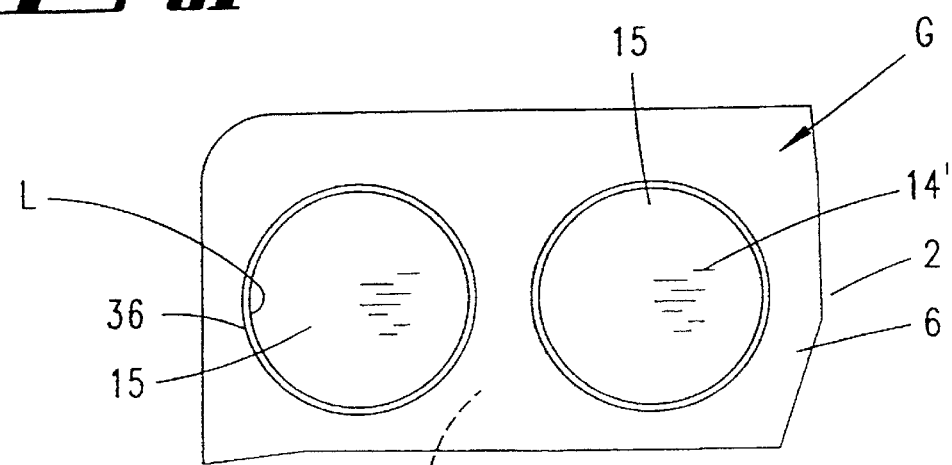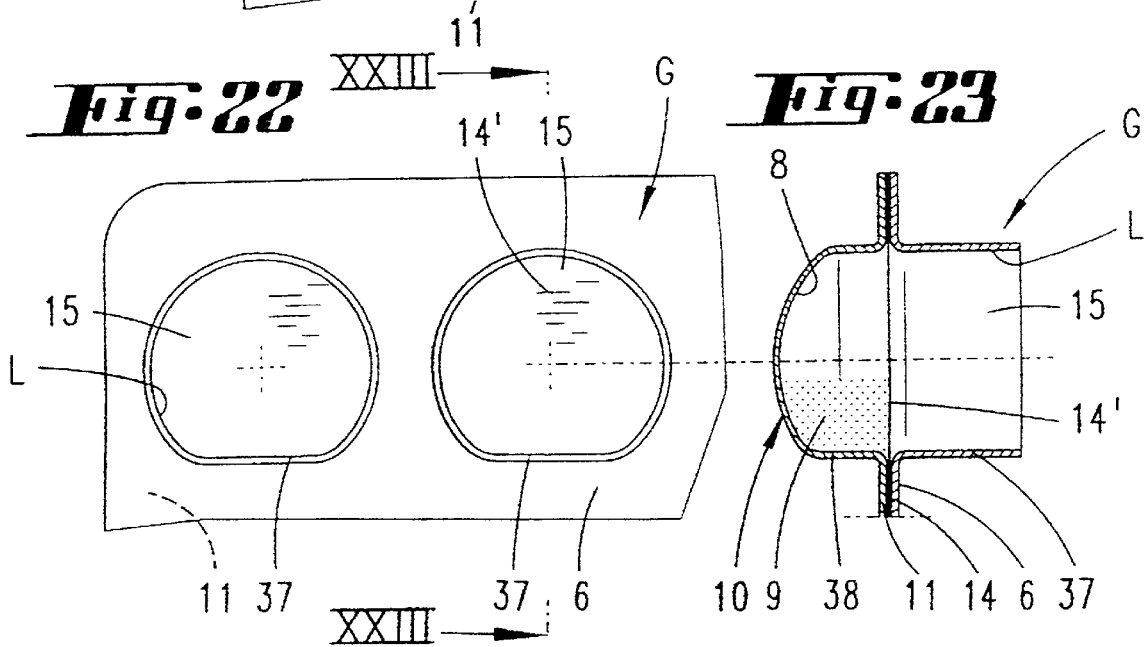

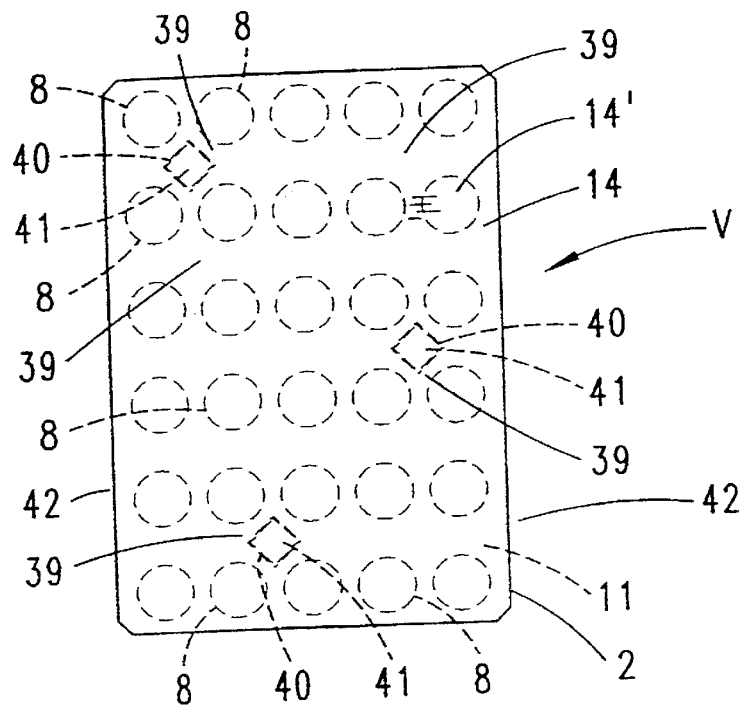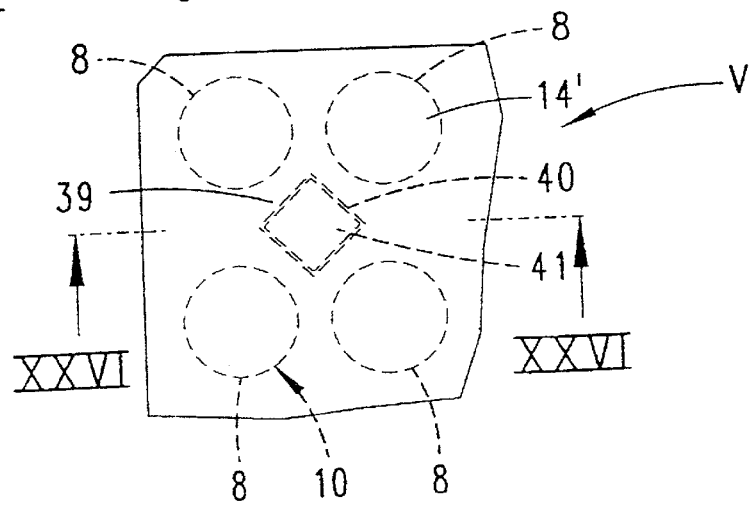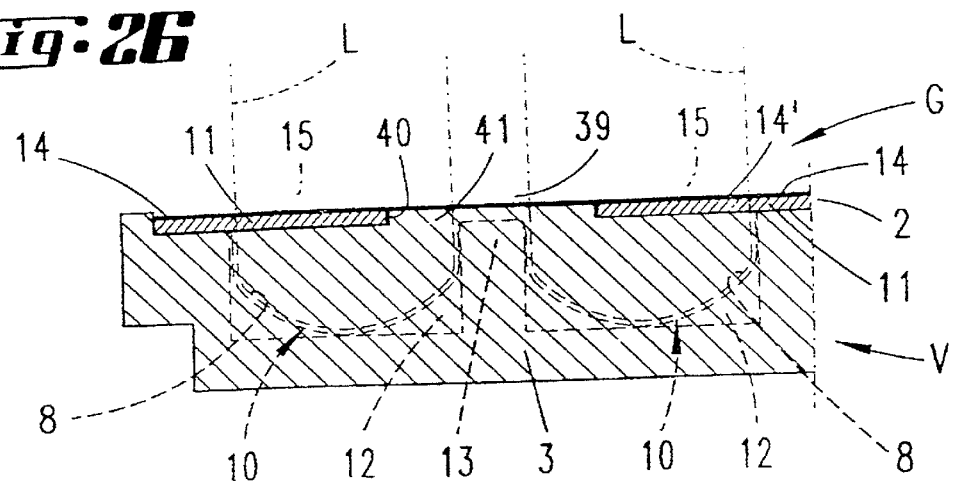

INHALER

The present invention relates to an inhaler, more particularly an inhaler for administering dry powder. It also relates to blister packs containing powder for use with the inhaler and to a method of dispensing powder from a blister.

It is known to provide certain medicaments in the form of a dry powder for inhalation for the treatment of respiratory conditions such as asthma.

It is also known to store individual doses separately in a sealed pack commonly known as a blister pack. The blister pack preferably comprises a series of moulded depressions each containing a dose of powder and sealed by a cover such as a foil. Either the user has manually to peel away the foil from an individual blister or a complex mechanism has to be provided to puncture the foil or cup-shaped part of the blister.

The task of finding the edge of a foil and peeling it away from the blister without spilling any of the contained powder can be difficult for some patients, for instance the young, the elderly or those actually experiencing an asthma attack. On the other hand, mechanisms for automatically opening a blister are complicated and therefore costly to produce. Furthermore, the automatic mechanisms do not peel the foil from the blister, but cut the foil or the cup-shaped portion of the blister itself. In some cases, this can give rise to the danger of parts of the foil or blister themselves becoming detached and joining the inhalation air stream. Furthermore, it has proved extremely difficult to cut the foil or blister in such a way as to ensure that all of the powder is removed from the blister or at least that a consistent proportion of the powder is removed.

According to the present invention there is provided an inhaler for administering dry powder, the inhaler comprising:
 an inhaler body extending between two ends;
 an outlet at one of said two ends;
 a suction tube at the other of said two ends; and
 an inhalation channel within said body providing fluid connection between said suction tube and said outlet; wherein
  the suction tube is shaped and dimensioned for insertion into a blister containing powder such that inhalation through the inhaler body will draw powder from the blister through the suction tube and inhalation channel and out of the outlet.

There is also provided a method of transferring powder from a blister to the outlet of a device, the device having an inlet connected to the outlet by means of a channel, the method comprising:
 inserting the inlet into the blister; and
 drawing air out of the outlet so as to form an air stream into the inlet and through the device, the airstream picking up powder from the blister and carrying it through the channel to the outlet.

Thus, there may be provided a device which is relatively simple to construct, of relatively low cost to the user, simple to use and yet extremely effective in removing powder from the blister.

Since the inhaler body is separate from the blister pack, it has the additional advantage of being easily cleaned either at regular intervals or when needed. The inhaler body may be cleaned in any way, including total emersion in water, without any danger of contaminating or interfering with the operation of the inhaler. This is in contrast with previous more complicated inhalation devices, where, even if the powder is sealed in blisters, any powder previously retained in other parts of the inhaler may not be fully removed from the more complicated parts of the inhalation device and may interfere with correct operation of the device by being dampened through a washing operation.

According to the present invention there is also provided an inhaler for administering dry powder from a blister sealed by a thin film cover, the inhaler comprising:
 a suction tube having an end for insertion into a blister; the end having:
  a channel inlet through which powder may be drawn; and
  a cutter around only part of the channel inlet such that, upon insertion into a sealed blister, the cutter cuts the film cover around only part of the channel inlet so as to form a cut film flap.

In this way, the cover foil of the blister is assuredly severed as necessary whilst ensuring that the cut portion of the cover remains attached to the rest of the cover. In this way, the cut cover cannot be inhaled by a user.

Preferably, the cutter comprises a plurality of axially extending blades divided by axially extending gaps.

In this way, it is assured that an air flow path exists from the blister to the channel inlet within the cutter, since air can always flow through the axially extending gaps. Furthermore, by virtue of the relationship between the blades and the gaps, the cover foil will tear to bridge the gaps between the cutters.

Preferably, the blades extend axially beyond the remainder of the end of the suction tube.

In this way, the blades first cut the cover foil, before pushing the cover foil away from the rest of the cover into the blister. The remainder of the end of the suction tube may come into contact with the cut cover foil at the last moments of insertion so as to assist in pushing the flap into the blister.

By using such a cutter, integral with the channel inlet, the blister is only cut when the suction tube is being fitted into the blister. In this way, penetration of the cover foil takes place while the suction tube is being fitted on such that fitting and sealing with the blister lasts throughout the period of use and any losses are avoided.

The present invention also provides an inhaler for administering dry powder from a blister sealed by a thin film cover, the inhaler comprising:
 a suction tube having:
  an end for insertion into a blister, the end having a channel inlet through which powder may be drawn; and
  at least one inlet passage extending between a passage inlet at a position along the length of the suction tube and a passage outlet adjacent said channel inlet, such that, with the end inserted into a blister, the inlet passage provides fluid connection between the blister and a space above the blister.

In this way, powder may be assuredly drawn from a blister, since inlet air channels are provided to the blister. In particular, those inlet air channels may be provided at the outer periphery of the blister so as to assist in ensuring that all of the powder in the blister is removed.

Preferably, the inhaler further comprises a support unit for supporting a blister pack, the support unit including respective guide portions for each blister of a supported blister pack, each guide portion being for guiding said suction tube into a respective blister and supporting the inhaler body with said suction tube so guided.

Alternatively, there may be provided a blister pack comprising at least one blister housing a dose of medicament, the blister comprising:

a cup-shaped portion for holding said powder;

a thin film cover for sealing the powder in the blister; and an axially elongate passage extending from said cup-shaped portion for guiding a suction tube of an inhaler into the blister.

In this way, it may be ensured that the inhaler body is correctly inserted into the blister. Since the inhaler body is guided into the blister, consecutive uses of the inhaler body will be more consistent. Furthermore, the user has a feeling of greater confidence in using it.

Where the blister pack is formed as a substantially planar surface with a series of depressions forming respective blisters, the support unit may include a guide wall to be positioned adjacent the substantially planar surface and having a series of apertures for alignment with the series of depressions, the guide wall extending away from the substantially planar surface so as to form the guide portions. The support unit may include a housing within which the blister pack may be contained, with the guide wall being a wall of the housing.

In this way, the blister pack is securely held in a housing convenient to the user with its blisters in alignment with the guide portions.

Preferably, the support unit includes a support member having a series of depressions for receiving the series of depressions of the blister pack such that in use each depression of the support member is located opposite a respective one of the series of apertures in the guide wall.

The support member may be moved in and out of the housing in any way, such as by a hinged mechanism, but, preferably, the support member is slidable in and out of the housing to load and unload blister packs in the support unit.

In this way, a blister may conveniently be loaded into or unloaded from the housing.

The support unit may include a holding section, such as a tray with a hinged lid, for holding the inhaler body when not in use.

This provides an extremely convenient overall inhaler for the user, enabling the inhaler body to be kept securely with the support unit.

The support member may have one or more projections or recesses with predetermined sizes and positions such that only blister packs with corresponding recesses or projections may be received by the support member.

In this way, it can be ensured that only the correct type of blister pack is used in the inhaler. For instance, a particular inhaler may be intended for a particular medicament. In this case, the support member could be shaped so as only to receive blister packs containing that particular medicament.

The shape of the inlet of the inhaler body and the guide portions of the support unit may also be specific to a particular type of inhaler, such that the inhaler body of one inhaler cannot be inserted into the guide portion of another inhaler.

In this regard, the present invention also provides a range of blisters, each comprising a depression sealed with a thin film cover and each housing a dose of respective medicament, the respective size and/or shape of each depression uniquely identifying the type of medicament within the respective depression.

It should be appreciated that the present invention is applicable with blister packs including any number of blisters, including only one.

Medicaments suitable for administration by using the present invention are any which may be delivered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolorie, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic- antiparasitic- and anticancer-medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N'-diacetylcystine.

The present invention will be more clearly understood from the following description, given by way of example only, with reference to the accompanying drawings, in which:

FIGS. 1, 2 and 3 respectively show top, end and side views of an inhaler housing;

FIG. 4 illustrates an inhaler body inserted into a guide portion of the inhaler housing;

FIGS. 5 and 6 respectively show perpendicular side views of the inhaler body;

FIG. 7 illustrates the cross-section VII—VII indicated in FIG. 6;

FIG. 8 illustrates the mouthpiece end of the inhaler body;

FIG. 9 illustrates the inlet end of the inhaler body;

FIG. 10 illustrates an enlargement of FIG. 9;

FIG. 11 illustrates the cross-section of the inhaler body and inhaler housing indicated by XI—XI in FIG. 4;

FIG. 12 illustrates the cross-section of the inhaler body indicated by XII—XII in FIG. 6;

FIG. 13 illustrates the cross-section of the inhaler body indicated by XIII—XIII in FIG. 5;

FIG. 15 illustrates a cross-section of the inhaler body inserted into a blister contained in the inhaler housing, but with a viewing angle perpendicular to that illustrated in FIGS. 11 and 14;

FIG. 16 illustrates the upper portion of an inhaler housing of another embodiment;

FIG. 20 illustrates a cross-section of the support unit on the blister pack indicated by XX—XX in FIG. 19;

FIG. 21 illustrates a top view of two of the guide portions of the support unit of FIG. 19;

FIG. 22 illustrates a variation of the support unit of FIG. 21;

FIG. 23 illustrates a cross-section through a guide portion and blister as indicated by XXIII—XXIII in FIG. 22;

FIG. 24 illustrates a blister pack having individualizing features outside the cup-shaped blisters;

FIG. 25 illustrates an enlargement of part of the blister pack of FIG. 24 illustrating an individualizing feature;

FIG. 26 illustrates a cross-section through the lister pack of FIGS. 24 and 25 as indicated by XXVI—XXVI in FIG. 25;

The basic operation of the preferred inhaler will be described with reference to FIGS. 1 to 4.

The inhaler comprises two main components, a blister pack container V and an inhaler body S. A protective covering may be provided for the container V.

Figure 18:
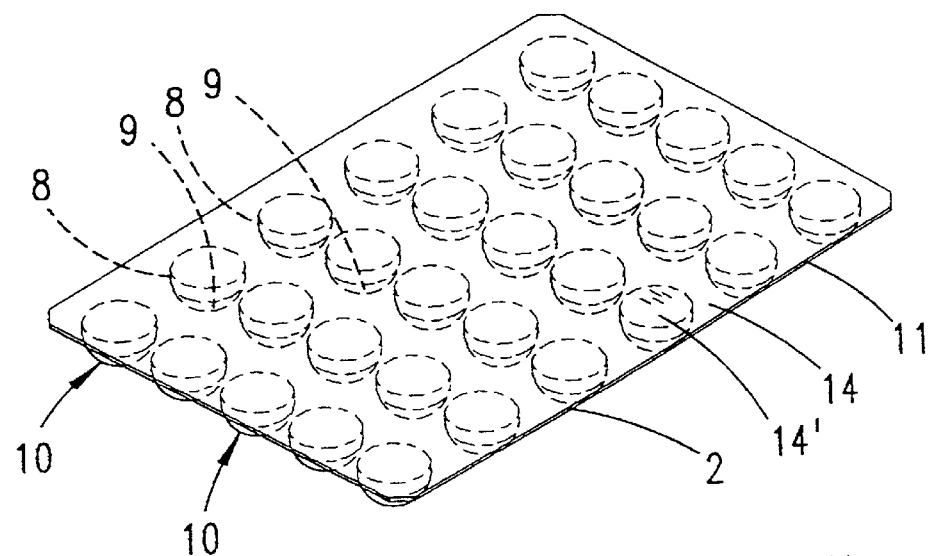
FIG. 18 illustrates a blister pack for use with an embodiment of the present invention.

The blister pack container V houses a blister pack, such as illustrated in FIG. 18, containing doses of powdered medicament. It has an array of guide portions L corresponding respectively to an array of blisters in the blister pack. It may be of a size similar to a tissue pack or cigarette pack.

The inhaler body S is preferably of a length which corresponds approximately to the small finger of an adult human hand and is normally housed in a chamber 34 to be described later. Having removed the inhaler body S from the chamber 34, its inlet end 19,20 is inserted into one of the guide portions L and pushed down into the container V so as to rupture the sealing foil of the respective blister contained beneath the respective guide portion L.

As will be described below, the inhaler body S includes an inhalation channel 31 which extends between the inlet 19,20 and a mouthpiece 17. Thus, with the inlet 19,20 inserted into a blister, a user may inhale from the mouthpiece 17 and through the inhalation channel 31 so as to draw the powder contained in the blister out through the inhaler body S which acts as an inhalation flow bridge. As will be apparent, successive doses are achieved by successively inserting the inhaler body S into a guide portion L corresponding to a previously unused respective blister.

As illustrated, the container V includes a housing 1 in which a blister pack is contained. Furthermore, in the preferred embodiment, it includes a chamber 34 in which the inhaler body S may be stored when not in use. As illustrated, the chamber 34 is closed by a lid 33 which may pivot open and closed by means of a hinge pin 35. The closing joint is obliquely running so that more gripping surface area remains on the closure cap or lid 33 with a corresponding overhang on the top wall side for better grasping. The joint is preferably at 45° with respect to the planar extent of the housing. Other arrangements are, of course, possible. For instance, the inhaler body S could be inserted axially into an opening in the side of the housing 1. In any arrangement, it is also possible to provide an elongate brush onto which the body S is fitted. In this way, whenever the body S is stored, it is not only held in place by the brush extending through its inhalation channel 31, but is also cleaned. Indeed, as the body S is pulled off the brush, it is cleaned immediately prior to use.

In order to prevent the body S and container V from being separated and one being lost, it is possible to provide a member, such as a cord for attaching one to the other. Preferably a very fine light cord like member should be used. This can be automatically retracted back into one or other of the body S and container V by means of a sprung mechanism. For example, the cord can be wound around a roller which unwinds against a relatively gentle resilient force.

The blister pack to be used in the inhaler is preferably similar to that illustrated in FIG. 18. This blister pack 2 has a generally planar, thin walled sheet body 11 in which depressions 8 are formed to contain powder 9. In particular, the depressions 8 are formed as cup-like portions 10. The sheet body 11 is then covered with a thin sheet 14, such as a foil, preferably aluminium, so as to form unsupported portions 14' which seal the powder 9 in the depressions 8.

As explained above, the blister pack 2 is located in the housing 1 such that individual blisters 8 are positioned directly beneath guide portions L. In particular, the housing 1 is provided with a substantially planar guide wall 6 against which the blister pack 2 is positioned. The guide wall 6 has apertures through its thickness so as to form the guide portions L and and guide the inlet portion 19, 20, of the inhaler body S to the unsupported cover foil 14' and receive the inlet portion such that it does not tilt. The guide portions may take the form of frames surrounding the unsupported portions 14' of the cover foil. However, in one embodiment the underside of the guide wall 6 is provided with elongate walls 6' which, as illustrated in FIG. 13, hold the blister pack 2 spaced apart from the lower surface of the guide wall 6. The elongate walls 6' are located between adjacent rows of guide portions L and extend across the width of the container V. They act to hold a blister pack 2 securely with respect to the guide wall 6 and the supporting tray 3 to be described below. However, by providing a space between the blister pack 2 and the guide wall 6 in the regions of guide portions L, the elongate walls 6' allow a good flow of air around and into any particular blister being used.

The blister pack container V preferably allows blister packs 2 to be replaced, such that a single inhaler may be used with successive blister packs 2 as they are emptied. It is possible to provide many different mechanisms for loading and unloading a blister pack 2 to and from the container V, such as by providing a hinged back. However, in the preferred embodiment, a slidable tray 3 is provided. The tray 3 slides in and out of one end of the housing 1 and is itself preferably provided with a series of depressions or cup receiving cavities 12 corresponding to the spacing of the cups 10 of the blister pack 2. In this way, the blister pack 2 may be laid onto the withdrawn tray 3 and be securely located such that when the tray 3 is inserted back into the housing 1, the blisters 8,10 and unsupported cover foils 14' are correctly aligned with the guide portions L. The cup receiving cavities 12 correspond, at least in outline, to the cups 10 of the blister pack 2 which, as illustrated are cylindrical in the region of attachment close to the top sheet. The cavities 12 form a crater structure ordered in the form of crisscrossing rows and partition walls 13 support the resting sheet body 11 by their end faces.

In order to facilitate removal of the tray 3, the illustrated embodiment is provided with a tab or handle 4 which protrudes into a recess 5 of the guide wall 6. As is apparent, the recess 5 is formed in the narrow-wall-side border region of the guide wall 6 without any overhang.

Preferably, the tray 3 is provided with some form of catch to secure it in the loaded position. This may be provided merely as a detent in opposing surfaces of the tray 3 and housing 1 or can be provided as part of the handle 4, such that the tray 3 is only released when the user deflects the handle 4 in some way.

As illustrated, in order to enable the tray 3 to be slid in and out of the housing 1, the housing 1 is provided with guides 7 having a generally C-shaped profile.

Before considering precisely how the inhaler body S interacts with the guide portions L and blister pack 2, we will consider the inhaler body S itself with reference to FIGS. 5 to 13.

As best illustrated by the cross-sections of FIGS. 12 and 13, the inhaler body S generally comprises an elongate body having an inlet at one end, a mouthpiece 17 with an outlet at the other end and an inhalation channel 31 providing fluid connection between the inlet and the outlet. In the preferred embodiment, the mouthpiece 17 and the outlet end of the inhaler body S are generally oval in shape, whereas the inlet end is generally circular in shape. As will become apparent from the following description, this is not essential, but does give rise to some added advantages. In particular, a flatly oval shaped mouthpiece is more comfortable in the mouth than a circular one. Furthermore, by shaping the inhalation channel 31 as illustrated such that it diverges from the inlet end to the outlet, a higher velocity air flow may be achieved at the inlet so as to improve both the collection of powder from the blister and deagglomeration of that powder.

As illustrated, despite the tapering of the inhalation channel 31, the general outer shape of the inhaler body S remains oval down most of its length, at least up to the shoulder 21. Indeed, its general overall shape only changes at the shoulder 21 for the portion 19 which is to be inserted into the guide portions L of the blister pack container V. The flats of the oval provide space for the finger tips of a gripping hand. In order to maintain the oval shape, ribs 18 are provided down the length of the inhaler body S. These are preferable features which provide the user with a convenient and secure means of gripping the inhaler body S. This is particularly useful, since a little force has to be applied to the inhaler body S when it is inserted into a guide portion L in order to rupture an unsupported cover foil 14'.

As illustrated, at the bottom of the series of ribs 18, just behind the supporting shoulder 21, inlets 32 are provided into the inhalation channel 31. These transverse air-admitting holes 32 are supplementary air inlets which allow additional air to be drawn into the inhalation channel 31 and mix with the air and powder mixture being drawn up the inhaler body S from its inlet. The provision of such supplementary air inlets 32 allows the user to inhale a less concentrated mixture of powder. Furthermore, the action of the supplementary air mixing with the air flow through the inhalation channel 31 provides some turbulence and assists in the deagglomeration of powder in the air stream. This effect is enhanced by the narrowing of the inhalation channel 31 as described above. Preferably, the cross-section of the two transverse air-admitting holes 32 together correspond approximately to the circularly round cross-section of the suction channel 31 in the bottom region.

Provision of the supplementary air inlets 32 adjacent the shoulder 21 is advantageous since, when the inhaler body S is positioned in a guide portion L, the surround of the guide portion L makes it extremely difficult for a user to block the supplementary air inlets 32 with his or her fingers.

The inlet end of the inhaler body S can be considered to comprise two parts, namely a suction tube 19 and an annular cutter 20.

The suction tube 19 is shaped to fit securely in the guide portions L, whilst allowing air to be drawn down around its sides into the ruptured blister below. As illustrated, it is matched cross-sectionally to the shape of hole 15 and may be circular so that an interruption free, well supporting contact with wall 6 is achieved. It forms a plug connection with frictional contact.

As described above, a shoulder 21 is provided separating the suction tube 19 from the upper parts of the inhaler body. This shoulder 21 in use rests in a tilt-preventing manner on the upper side of the guide wall 6 and thus also abuts the guide wall 6 so as to ensure that the suction tube 19 is always inserted into the guide portion L and associated blister 8,10 by the same amount. The suction tube 19 is, of course, chosen to be of a length which positions its end at the location in a blister most suited to withdrawing powder.

Figure 4:
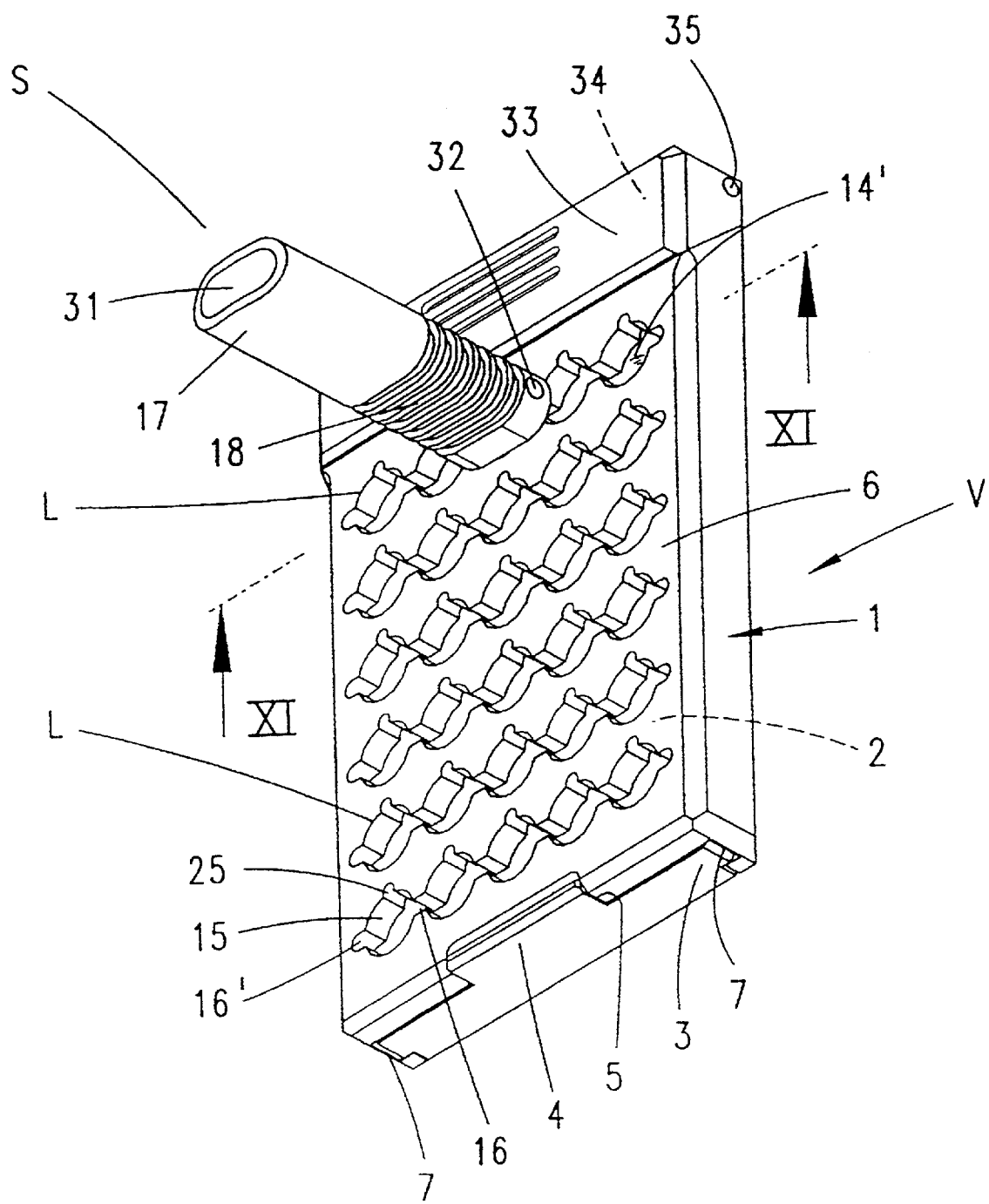
Figure 14:
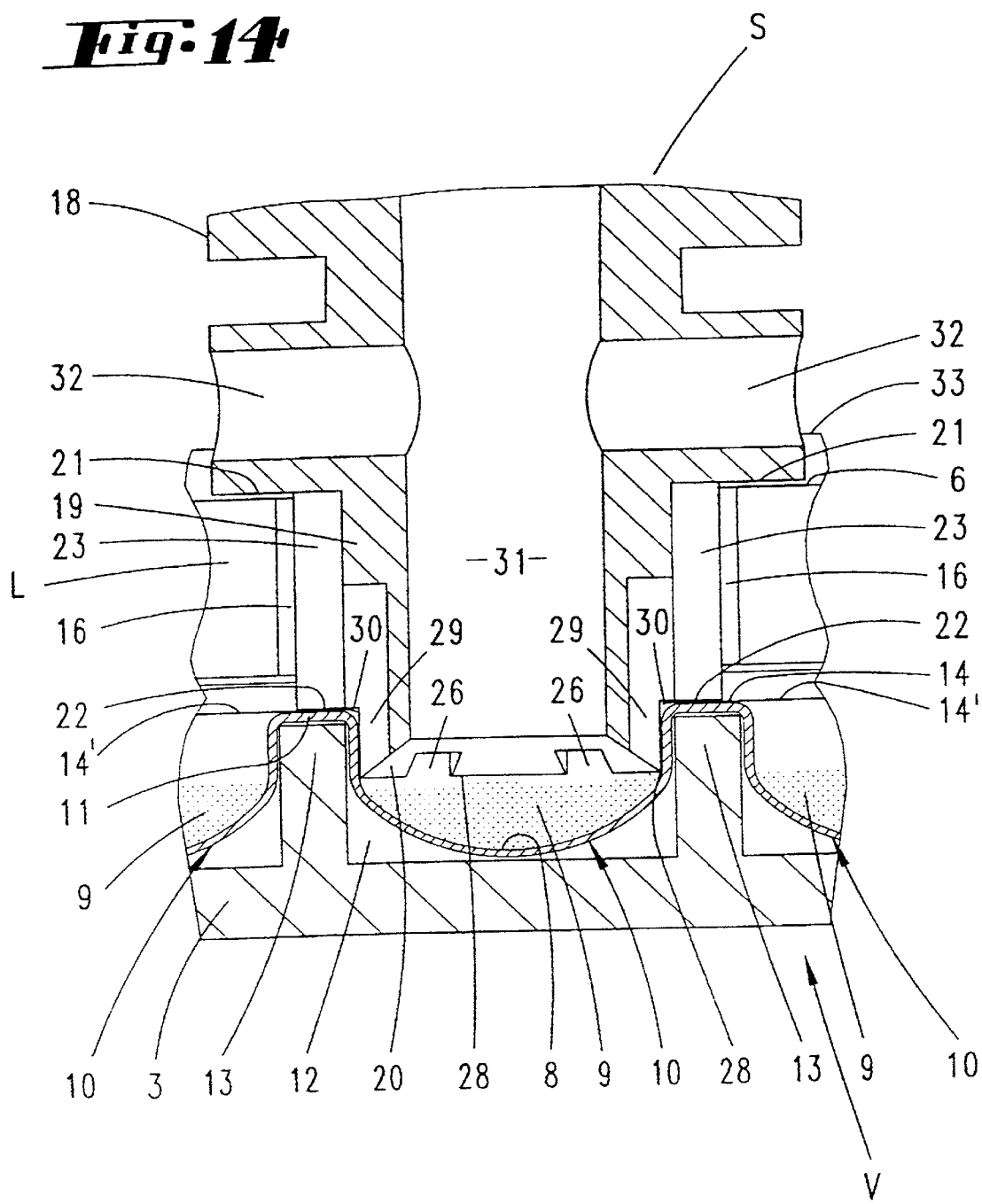
FIG. 14 illustrates the inlet of the inhaler body inserted into a blister contained in the inhaler housing.

A feature of the suction tube 19 is the provision of air inlet channels 29 formed in its outer thickness and running down along its length. As will become apparent below and, indeed, as illustrated in FIG. 14, these channels 29 provide an air path from above the surface of the blister pack down to a position below the ruptured cover foil 14'. In other words, during inhalation through the inhaler body S, air is drawn down through the air inlet channels 29 into the blister 8,10 to pick up the powder 9. The resulting air/powder mixture then continues up into the suction tube 19 and through the inhalation channel 31.

As illustrated, the annular cutter 20 is provided on the end of the suction tube 19. It has a number of cutting blades 28 arranged around a greater part of its outer periphery. The cutting blades are themselves separated from one another by gaps 26. In the illustrated embodiment, four gaps 26 are provided to form three annular cutting blades 28. The remaining fourth segment between the gaps 26 is not provided with a blade. As illustrated in FIGS. 5 and 15, this segment tapers up towards the top surface of the blister 8,10. Indeed, the annular cutter 20 may generally be angled relative to the axis of the inhaler body S such that the cutting blade 28 opposite the segment without a cutting blade contacts the cover foil 14' of the blister pack 2 before the other cutting blades 28.

As will be apparent from the figures, when the suction tube 19 is inserted into a guide portion L, the cutting blades 28 of the annular cutter 20 will come into contact with an unbroken cover foil 14'. Upon pushing the inhaler body S further into the guide portion L, the cutting blades 28 will start to cut the cover foil 14'. Of course, where the gaps 26 occur, the cover foil 14' will not as such be cut by a blade 28. However, the gaps 26 are of a size relative to the blades 28 and blister 8,10, such that the cover foil 14' will easily tear so as to provide a continuous cut in the cover foil 14' between the blades 28. As mentioned above, the blades 28 of the annular cutter 20 do not extend around the entire annulus of the suction tube 19, but leave a segment, preferably of about 90°, which does not cut the cover foil 14'. Indeed, it does not start to come into contact with the cover foil 14' until the cutting blades 28 have cut the cover foil 14' and have been inserted into the volume of the blister 8,10. The cutting blades 28 are merely sharpened edges of the full thickness of the annular cutter 20 and are positioned at the outer edge of the thickness of the annular cutter 20. Therefore, as the suction tube 19 is pushed further into the blister 8,10, the annular cutter 20 pushes with it the cut cover foil 14'. That section of the cover foil 14' which is not cut thus acts as a hinge 27. In other words, there is left a virtually hinge-forming bridge between the valve flap-like punched free tabs of the unsupported portion 14' and the bordering zone of the unsupported portion 14'. With the suction tube 19 fully inserted into the blister 8,10, the segment of the annular cutter 20 without blades 28 can come into contact with the foil, but then only to ensure that the cut cover foil 14' is pushed down into the blister 8,10, thereby ensuring that the inhalation channel inlet formed in the centre of the annular cutter 20 is open to the interior of the blister 8,10.

Preferably, the cover foil 14' is cut so as to leave the hinge at an upper side as viewed in FIG. 1. This is because, in normal use, the device will be held with a blister pack tilted down from the far end such that powder in individual blisters will collect away from the hinge for easy removal.

It will be appreciated that the cutting and insertion arrangement ensures that reliable and consistent cutting of cover foils 14' always occurs, whilst also ensuring that the cut cover foil 14' cannot, because of the hinge 27, be carried into the inhalation air stream of the user. The interruptions of the radially inwardly undercut blade 28 achieves peripheral longitudinally directed air-inlet channels 29 which cannot be blocked by the cover foil material, as air-inlet cross-sections. The channels 29 in the sides of the suction tube 19 ensure that air is effectively drawn into the blister 8,10 under the cover foil 14. They also direct the inlet air into the outer periphery of the blister 8,10 at a number of positions so as to ensure that powder 9 throughout the blister 8,10 is exposed to the flow of air. The gaps 26 on the other hand ensure that the resulting air-powder mixture will always be able to flow past the cut cover foil 14' up into the inhalation channel 31.

Returning to FIGS. 1 and 4, it will be noted that the guide portions L are not formed merely as simple circular holes, but are formed as holes 15, with radial extensions 16,16' and 25. Indeed, to use the space available most efficiently, horizontally adjacent holes 15 share extensions, such that they are joined by common extension 16.

Corresponding to those extensions 16,16' and 25, the suction tube 19 of the inhaler body S is provided with protrusions 23 and 24, as illustrated in FIGS. 5 and 6. FIG. 14 illustrates how the protrusions 23 fit into the extensions 16 (or 16'). It is self evident how, similarly, the protrusion 24 (not shown in FIG. 14) fits into the extension 25.

The corresponding extensions 16,16',25 and protrusions 23,24 hold an inserted inhaler body S more securely in a guide portion L and therefore make the inhaler easier and more pleasing to use.

The use of an asymmetric arrangement of extensions and protrusions means that the inhaler body S may only be inserted with one particular predetermined orientation. This provides more consistent and pleasing operation for the user. Furthermore, if the blisters have a non-symmetric cup shape, then this is also advantageous for the reason that it ensures that the suction tube 19 is always inserted with the correct orientation.

Irrespective of the nature of the blisters, ensuring that the inhaler body S is always inserted with the same orientation has the following advantage. The user is only able to insert the suction tube 19 of the inhaler body S into a previously used blister with the same orientation as was previously used. If a user accidentally inserts the suction tube 19 of the inhaler body S into a previously used blister and inserts it with the opposite orientation to that used previously, then the cut cover foil 14' can become completely detached, thereby allowing the user to inhale it. However, with the arrangement described above, this is not possible.

As illustrated in FIG. 14, the protrusions 23 abut the top surface of the blister pack 2. Indeed, a shoulder 22 is provided to abut the blister pack 2 and the protrusions 23 and 24, where provided, form part of this abutting shoulder. The abutment of the shoulder grips the blister pack against the upper side of the partition wall 13, circumscribing the cup receiving cavity 12. In this way, it is ensured that, irrespective of the position of the shoulder 21, variations occurring for instance for tolerance reasons, the annular cutter 20 and suction tube 19 will not be inserted too far into a blister 8,10. This is particularly important, since, if the suction tube 19 were inserted too far, the segment of the annular cutter 20 without blades 28 might tear and detach the cover foil 14'.

Of course, it is possible to use many other different shapes for the guide portions L. FIG. 16 illustrates one possibility, namely the use of holes 15 with flattened sides 37. Such arrangements can replace the protrusions and extensions above in fixing the relative orientation of the inhaler body S and guide portions L. Preferably, the flattening 37 lies on a side diametrically opposite the film hinge 27 parallel thereto. This leads to an even shorter valve-flap-like freeing cut. The opening region at the end face of the suction tube 19 is thus kept even more free. Moreover, due to gravity, the material accumulates in front of the free end of the flap, powder 9 taking up a small proportion of the volume of the cup.

Figure 17:
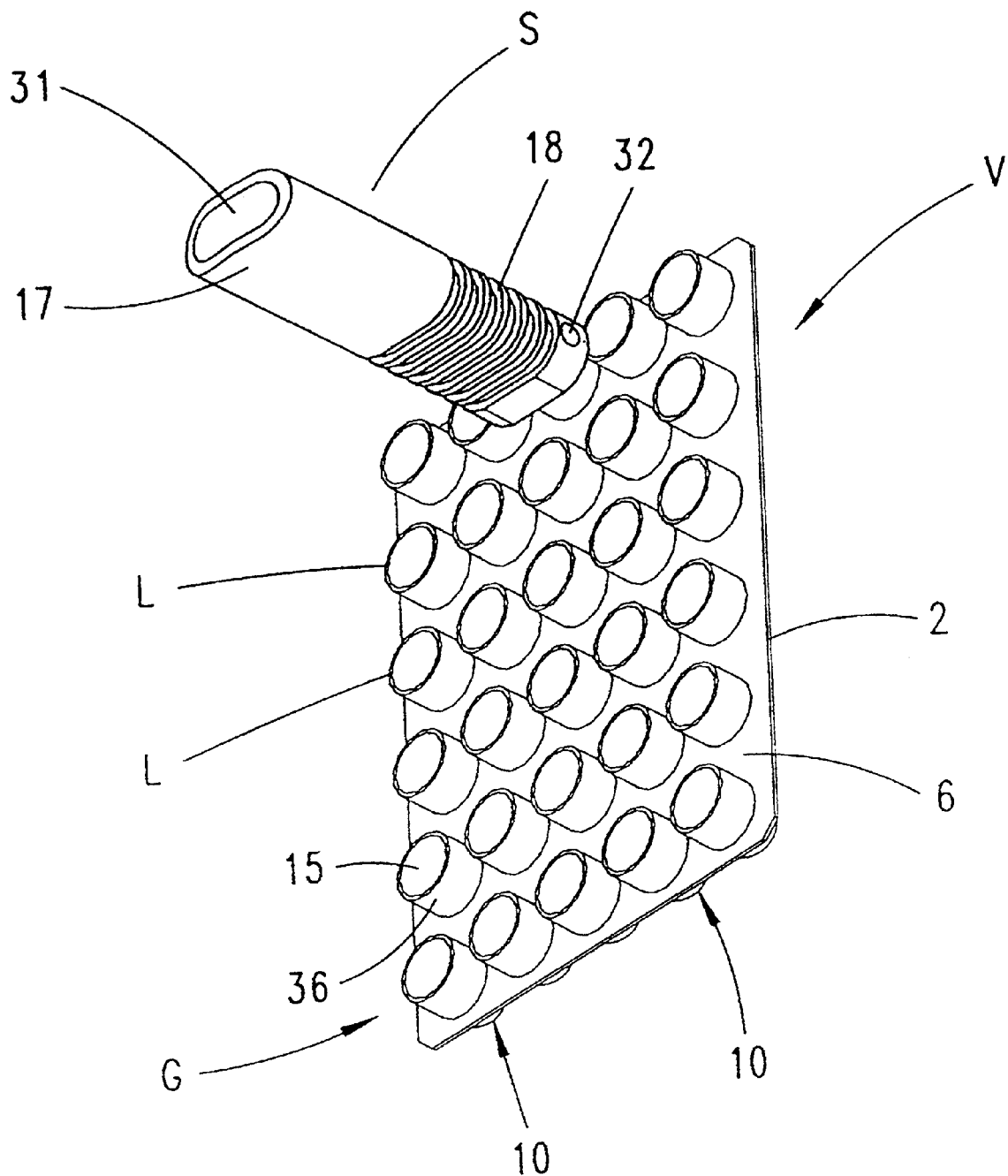
FIG. 17 illustrates an inhaler body inserted into a support unit according to another embodiment.

So far, the invention has only been described with relation to a blister pack container V. However, it is also possible to provide an equivalent device G such as illustrated in FIG. 17, which does not contain the blister pack 2.

The device G basically comprises a guide wall 6, such as the guide wall of the previous embodiment, with stubs 36 forming the holes 15 of the guide portions L. The stubs 36 receive the suction tube 19 such that it does not tilt. The device G can be produced from a plastics material.

Figure 19:
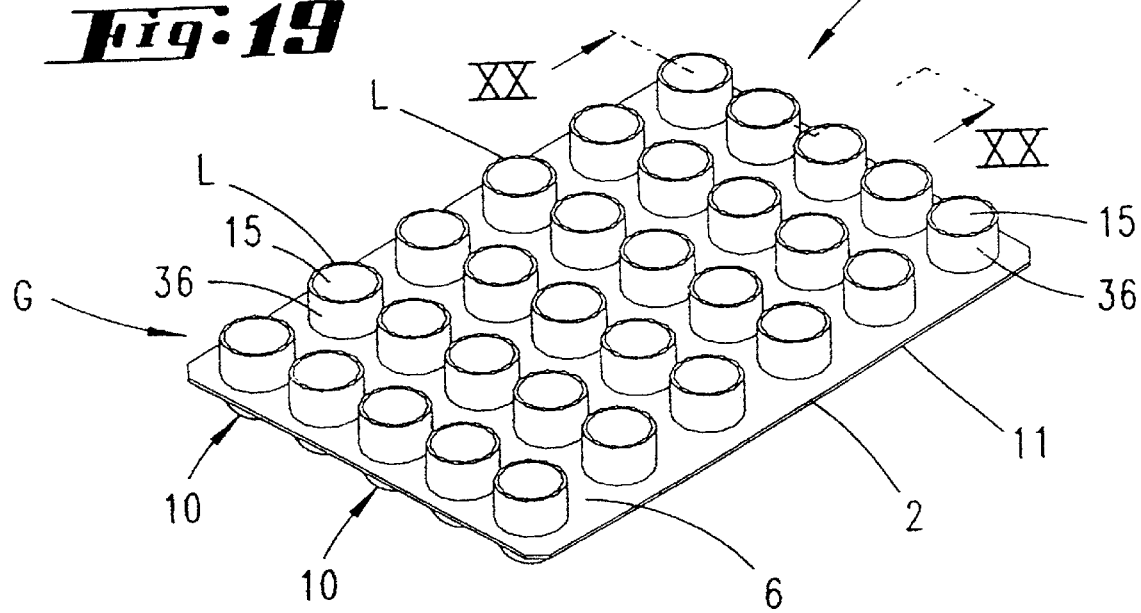
FIG. 19 illustrates the support unit of FIG. 17 adjacent the blister pack of FIG. 18.

The device G can be embodied in two functionally equivalent but commercially different ways. It can be provided as an integral part of a blister pack as illustrated in FIG. 19 or, as with the previous embodiment, as a separate device for use with successive blister packs 2.

When the device G is produced as part of the blister pack itself, the guide wall 6 can be fixed to the covering foil 14, for instance by adhesive or heat sealing. However, when the device G is produced as a separate item, it is preferably provided with some means of releasably securing a blister pack to its back surface and holding it in the correct relative position. For example, three of the four edges of the device G could be provided with generally C-shaped lips, such that a blister pack could be slid into position on the device G from the edge without such a lip.

Functionally, the device G is used in the same way as container V. In particular, the suction tube 19 and annular cutter 20 of an inhaler body S are inserted into the opening 15 of the guide portion L so as to rupture all but a hinge 27 of the cover foil 14'.

Rather than have a chamber such as used with the container V, the device G can be provided with one or more clips, for instance resilient claws, for attaching the body S to it.

In the illustrated embodiment, the guide portions L are not provided with extensions. Therefore, the suction tube 19 of the inhaler body S is similarly not provided with protrusions. However, it is of course possible to provide other embodiments with protrusions/extensions or shaping of the guide portions L as described previously. In this respect, the embodiment of FIGS. 22 and 23 differs slightly from that of FIGS. 20 and 21 in that, like the embodiment of FIG. 16, a flattened portion 37 is provided on the opening 15 to ensure that the inhaler body S is always inserted with the same orientation.

Both the embodiment of FIGS. 20 and 21 and the embodiment of FIGS. 22 and 23 illustrate the use of stubs 36 with the same cross-section as the upper portion of the blisters 8,10. In particular, the blister 8,10 of FIG. 23 has a flattened portion 38 matching the flattened portion 37 of the stub 36. However, it is not necessary for a stub 36 to be the same shape as its blister 8,10. It is desirable for those parts of the suction tube 19 inserted into a blister 8,10 to cover substantially all of the area of the blister 8,10 so as to lift all of the powder 9 from that blister 8,10. However, other portions of the suction tube 19 and inhaler body S may extend beyond the periphery of the blister 8,10. In this way, the shape and/or size of the stub 36 may be freely varied. Indeed, if the stubs 36 are at least partially larger than the blisters 8,10, a shoulder, such as shoulder 22 described for the previous embodiment may be provided on the inhaler body S.

Before moving on, it should be noted that the variation in the shape and size of the guide portions L, whether in the holes 15 or stubs 36, has another significant advantage. The shape of the guide portions L may be chosen according to the medicament to be dispensed. In this way, inhaler bodies S can be shaped according to the medicament with which they are intended to be used. Although the basic design of the inhaler body S is suitable for use with any medicament, it is preferable that a single inhaler body S is not used with different types of medicament. Thus, for a user who has to administer two or more types of medicament, by shaping the inhaler body 9 and guide portions L uniquely according to the type of medicament, there will be no possibility of the user inadvertently using the inhaler body S with a different medicament.

Where a device G is adhered to blisters, any shaping of the guide portions L, whether for distinguishing orientation, medicament or both is necessarily fixed relative to the blisters. However, for devices for use with the present invention where blister packs may be interchanged, it then becomes important that the user always positions the blister pack relative to the device with the same orientation and/or only uses the device with blister packs containing the correct medicament. The present application therefore proposes a blister pack which not only includes a number of sealed blisters, but also includes some means of distinguishing the orientation and/or contents of the blister pack.

It is conceivable, in an electronically controlled device, to provide a blister pack with some form of electronically readable information, for instance in the form of a magnetic strip or optical bar coding. In order to provide a distinguishing feature with a simple mechanical system, it is proposed to provide the blister pack with portions having particular shapes, sizes and positions to distinguish orientation/medicament type. In particular, to distinguish orientation, the features should be asymmetric with respect to rotation of the blister pack between its otherwise possible insertion orientations.

FIGS. 24 to 26 illustrate a blister pack where the planar sheet 11, in the intermediate zones 39 of the circularly round, cup-shaped depressions 8, is formed with three openings 40 in a specific distribution which, in the illustrated embodiment, are still covered by the cover foil 14. These areas are placed in terms of their centre point at the corners of a square or rectangle. This embodiment is particularly well suited to the embodiment of FIG. 1 where the blister pack is laid on a tray 3 before being inserted into the blister pack container V. As illustrated in FIG. 26, in this case, the tray 3 is provided with protrusions 41 corresponding in size, shape and position to the openings 40 of the blister pack 2. In this way, when the blister pack is laid onto the tray, with its blisters 8,10 in the corresponding recesses of the tray 3, the protrusions 41 fit into the openings 40. As is apparent from FIG. 24, if the blister pack 2 were to be laid on the tray 3 with the opposite orientation, the protrusions 41 of the tray 3 would not align with the openings 40 of the blister pack 2, such that the blister pack 2 would stand proud of the tray 3 and prevent insertion into the blister pack container V. In the illustrated embodiment, it will be seen that there are twenty intermediate zone regions 39 in which to form openings, thereby allowing great possibilities for variations in combinations. Covering of the openings 40 with the foil 14 is advantageous since the openings are thus hidden from sight.

The shape, positioning or size of the openings 40 in the blister pack 2 may also be used to distinguish a particular medicament. In this way, if a blister pack is used with a tray 3 having protrusions corresponding to a different medicament, the blister pack 2 will again stand proud and prevent insertion.

Figure 27:
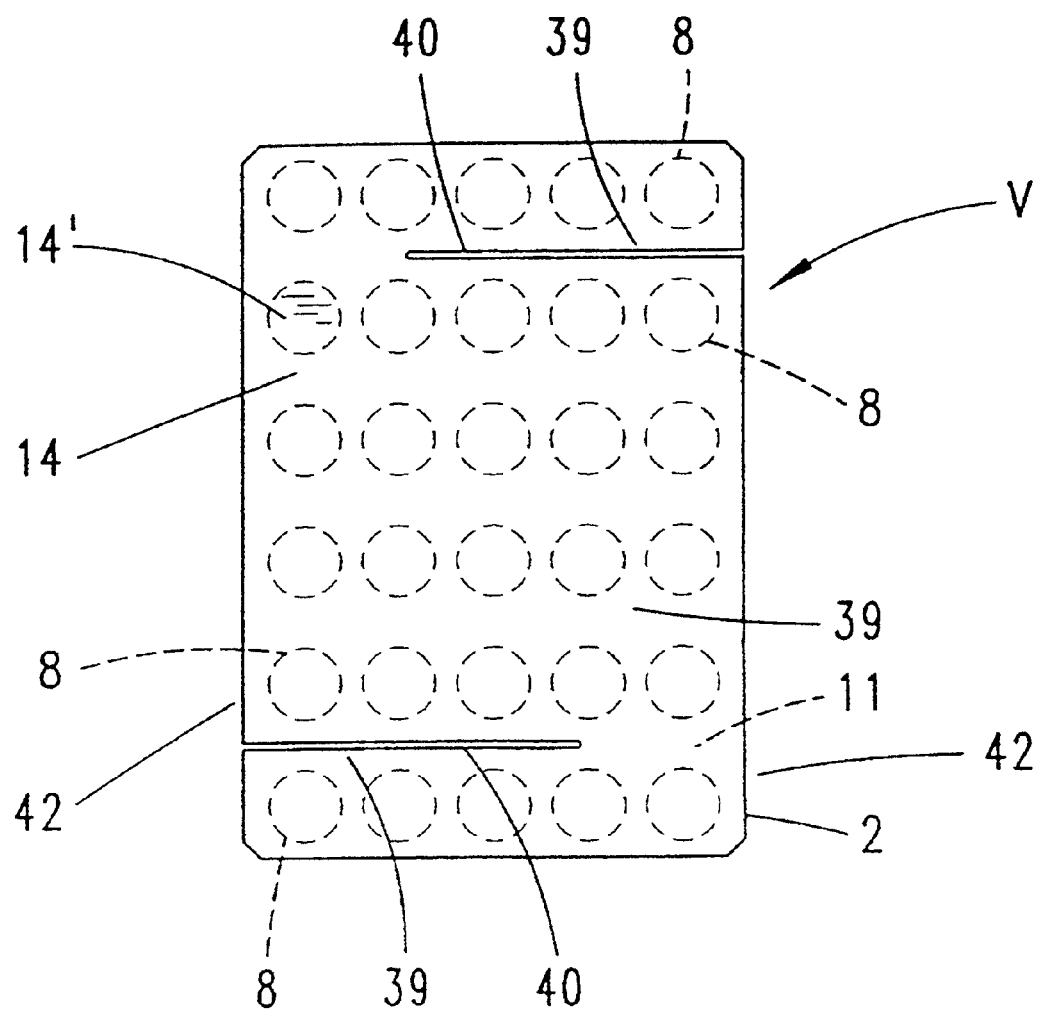
FIG. 27 illustrates a blister pack with an alternative form of individualizing feature.

The openings 40 and projections 41 described above have a lozenge-shaped or square outline. However, variations are of course possible, such as the provision of slits 40 extending from the border 42 as illustrated in FIG. 27. The illustrated slits are aligned such that they run oppositely. They extend parallel to the narrow sides of the long-rectangular basic outline of the packaging sheet 2. The length of the slits is greater than half of the length of the narrow sides. Accordingly, the slits overlap each other in the central region of the packaging sheet 2. The arrangement of the slits is paracentral. The male die parts associated with this type of openings 40 are of a correspondingly web-like shape or blade like form and extend from the base 3 of the device. Also, as with other embodiments, the cover foil 14 can be broken to correspond with the openings 40.

The blister pack could be provided with the protrusions, for instance as small redundant appropriately positioned blisters. Indeed, the protrusions could be provided as thermoformed projections like the cups 10. Alternatively, the shape and positioning of the blisters themselves could distinguish orientations and/or medicament types.

For devices G for use with successive blister packs, the protrusions/recesses can be provided on the cover foil 14 face of the blister pack 2 and the opposing face of the device G. For the embodiment mentioned with C-shaped lips on opposing edges, it would also be possible to taper the width of the device G and blister pack 2 from one end to the other, such that it would only be possible to insert the blister pack 2 into the device G narrow end first.

Figure 28:
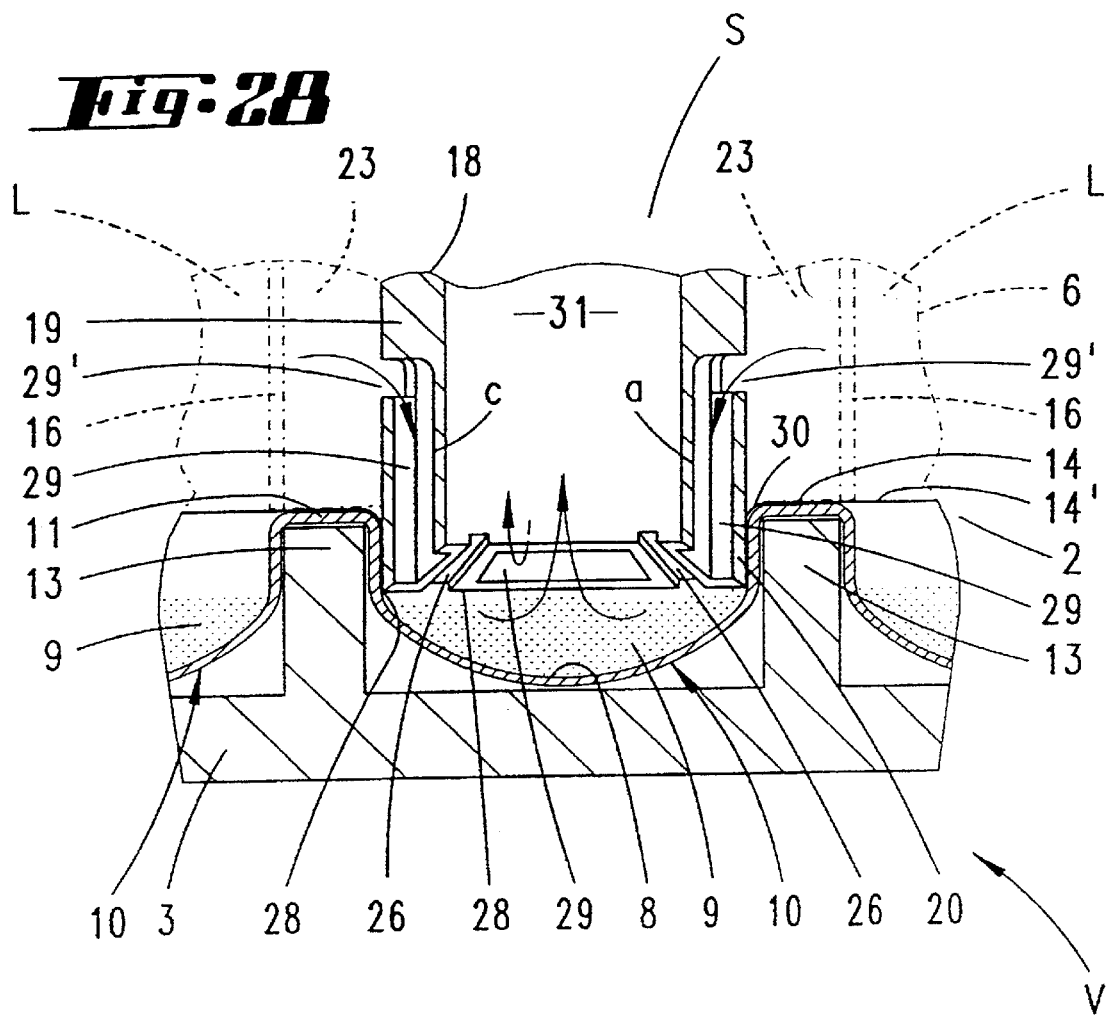
FIG. 28 illustrates a cross-section of a variation of the inlet of an inhaler body as indicated by XXVIII—XXVIII in FIG. 29.
Figure 29:
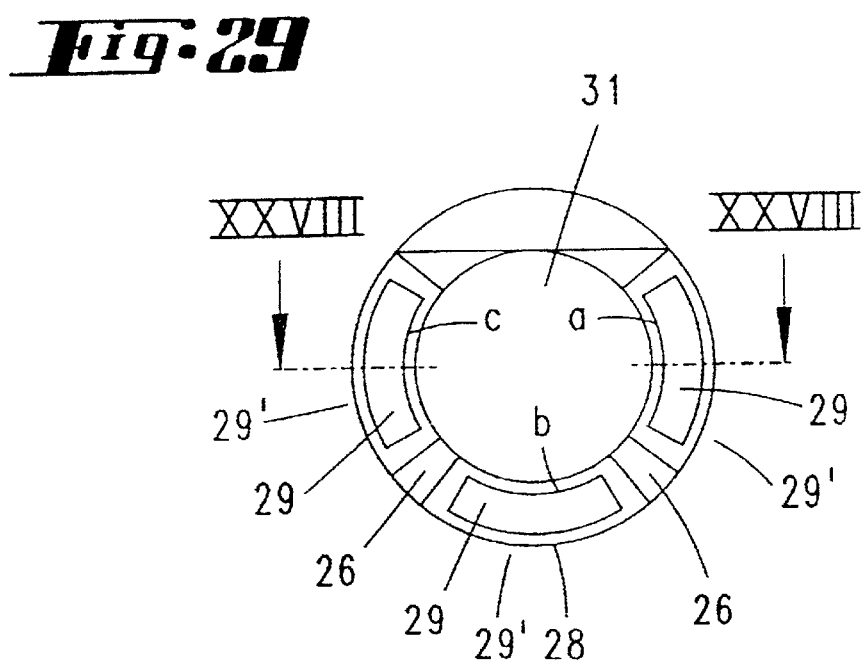
FIG. 29 illustrates a view of the inlet of the inhaler body of FIG. 28.

FIGS. 28 and 29 illustrate a variation to the suction tube 19 of the inhaler body S which is applicable to any of the previously described embodiments. In this variation, the air inlets 29 are not channels down the side of the suction tube 19 terminating at the gaps 26 of the annular cutter 20, but are enclosed channels in the walls of the suction tube 19 having broad outlets adjacent the cutting blades 28 between the gaps 26, air being drawn in through openings 29' in the side of the suction tube 19. The outlets are ring-sector portions, denoted by a, b and c. This variation has the advantage of providing a flow of air into the blister 8,10 around a greater periphery of the blister.

What is claimed is:

1. An inhaler for administering dry powder, the inhaler comprising:
   an inhaler body (S) extending between two ends;
   an outlet (17) at one of said two ends;
   a suction tube (19,20) at the other of said two ends; and
   an inhalation channel (31) within said body (S) providing
      fluid connection between said suction tube (19,20) and said outlet (17); wherein
      the suction tube (19,20) is shaped and dimensioned for insertion into a blister pack containing powder such that inhalation through the inhaler body (S) will draw powder from the blister through the suction tube (19,20) and inhalation channel (31) and out of the outlet (17);

the inhaler further comprises a support unit (V, G) for supporting a blister pack (2), the support unit (V,G) including respective guide portions (L) for each blister of a supported blister pack (2), each guide portion (L) being for guiding said suction tube (19,20) into a respective blister and supporting the inhaler body (S) with said suction tube (19,20) so guided;

a substantially planar surface having a series of depressions (10) forming respective blisters, the support (V,G) including a guide wall (6) to be positioned adjacent said substantially planar surface opposite said depressions and having a series of apertures (15,16) for alignment with the series of depressions, the guide wall (6,36) extending away from said substantially planar surface so as to form said guide portions (L,36); and wherein the suction tube has an inlet section configured for successive removal from and insertion into the blister pack, the blister pack having a plurality of blisters, each aperture serving to guide the inlet section of the suction tube into a respective blister of the blister pack and supporting the suction tube when so guided from blister to blister by a user of the inhaler.

2. An inhaler for administering dry powder, the inhaler comprising:

an inhaler body (S) extending between two ends;
an outlet (17) at one of said two ends;
a suction tube (19,20) at the other of said two ends; and
an inhalation channel (31) within said body (S) providing fluid connection between said suction tube (19,20) and said outlet (17); wherein
the suction tube (19,20) is shaped and dimensioned for insertion into a blister pack containing powder such that inhalation through the inhaler body (S) will draw powder from the blister through the suction tube (19,20) and inhalation channel (31) and out of the outlet (17);
the inhaler further comprises a support unit (V, G) for supporting a blister pack (2), the support unit (V,G) including respective guide portions (L) for each blister of a supported blister pack (2), each guide portion (L) being for guiding said suction tube (19,20) into a respective blister and supporting the inhaler body (S) with said suction tube (19,20) so guided;
a substantially planar surface having a series of depressions (10) forming respective blisters, the support (V,G) including a guide wall (6) to be positioned adjacent said substantially planar surface opposite said depressions and having a series of apertures (15,16) for alignment with the series of depressions, the guide wall (6,36) extending away from said substantially planar surface so as to form said guide portions (L,36);
wherein the support unit (V) includes a housing (1) within which the blister pack (2) may be contained, the guide wall (6) being a wall of said housing (1); and
the support unit (V) includes a support member (3) having a series of depressions (12) for receiving the series of depressions of the blister pack, in use, each depression (12) of the support member (3) being located opposite a respective one of said series of apertures (15) in said guide wall (6).

3. An inhaler according to claim 2 wherein the support member (3) is slidable in and out of the housing (1) to load and unload blister packs (2) in the support unit (V).

4. An inhaler according to claim 2 wherein the support member (3) has one or more projections (41) or recesses with predetermined sizes and positions such that only blister packs (2) with corresponding recesses (40) or projections may be received by the support member (3).

5. An inhaler according to claim 4 wherein said one or more projections (41) or recesses (40) are positioned and/or sized such that said blister packs may only be received with a predetermined relative orientation.

6. An inhaler for administering dry powder, the inhaler comprising:

an inhaler body (S) extending between two ends;
an outlet (17) at one of said two ends;
a suction tube (19, 20) at the other of said two ends; and
an inhalation channel (31) within said body (S) providing fluid connection between said suction tube (19, 20) and said outlet (17); wherein
the suction tube (19, 20) is shaped and dimensioned for insertion into a blister pack containing powder such that inhalation through the inhaler body (S) will draw powder from the blister through the suction tube (19, 20) and inhalation channel (31) and out of the outlet (17);
the inhaler further comprises a support unit (V, G) for supporting a blister pack (2), the support unit (V,G) including respective guide portions (L) for each blister of a supported blister pack (2), each guide portion (L) being for guiding said suction tube (19, 20) into a respective blister and supporting the inhaler body (S) with said suction tube (19, 20) so guided, the support unit also including a series of apertures;
said suction tube (19, 20) and each of said apertures (15, 16) within said series of apertures are shaped such that said suction tube (19, 20) can only be inserted through any one of said apertures (15, 16); and
each of said apertures (15, 16) is generally circular in shape with at least one radial extension (16, 16').

7. An inhaler according to claim 6, wherein at least some of said apertures (15, 16) are joined together by way of the at least one radial extension (16, 16').

8. An inhaler according to claim 6, wherein the support unit (V) includes a holding section for holding said inhaler body (S) when not in use.

9. An inhaler according to claim 8 wherein the holding section comprises a tray with a hinged lid.

10. An inhaler according to claim 6, wherein a channel inlet is formed in the end of the suction tube (19) and the end of the suction tube (19) has a cutter (20) formed around only a part of the channel inlet such that, upon insertion into a sealed blister (8), the cutter (20) cuts a film cover (14') of the blister (8) around only part of the channel inlet so as to form a cut film flap (14').

11. An inhaler according to claim 10 wherein the cutter (20) comprises a plurality of axially extending blades (28) divided by axially extending gaps (26).

12. An inhaler according to claim 11 wherein the blades (28) extend axially beyond the remainder of the end of the suction tube (19).

13. An inhaler according to claim 11 wherein the passage outlet is located at one of said gaps (26).

14. An inhaler according to claim 11 wherein the passage outlet is located between two of said gaps (26).

15. An inhaler according to claim 10 wherein the cutter (20) is formed around the outer periphery of the suction tube (19) such that, when the suction tube (19) is inserted into a blister (8), the inner periphery of the suction tube (19) pushes the cut film flap (14') into the blister (8).

16. An inhaler according to claim 10 wherein the suction tube (19) has at least one inlet passage (29) extending between a passage inlet (29') at a position along the length of the suction tube (19) and a passage outlet adjacent said channel inlet, such that, with the end inserted into a blister (8), the inlet passage (29) provides fluid connection between the blister (8) and a space above the blister (8).

17. An inhaler according to claim 16 wherein the passage outlet is located adjacent the cutter (20).

18. An inhaler according to claim 6, wherein a channel inlet is formed in the end of the suction tube (19) and the suction tube (19) has at least one inlet passage (29) extending between a passage inlet (29') at a position along the length of the suction tube (19) and a passage outlet adjacent said channel inlet, such that, with the end inserted into a blister (8), the inlet passage (29) provides fluid connection between the blister (8) and a space above the blister (8).

19. An inhaler according to claim 6, wherein, at a predetermined distance from said channel inlet, the suction tube (19) includes a radial extension for use as a shoulder (22) against the periphery of a blister (8) to prevent the end of the suction tube (19) from being inserted too far into the blister (8).

20. An inhaler according to claim 6, in combination with the blister pack.

21. A blister pack comprising at least one blister housing a dose of medicament, the blister comprising:
a cup-shaped portion (8) for holding powder;
a thin film cover (14') for sealing the powder in the blister (8);
an axially elongate passage (36) extending from said cup-shaped portion (8) for guiding a suction tube of an inhaler into the blister (8); and
a suction tube (19) for insertion into the elongated passage (36); wherein
the cross-section of the elongated passage (36) corresponds to the cross-section of at least part of the suction tube (19), such that the elongated passage (36) securely guides the suction tube (19) into the blister (8); and
said cross-section is of predetermined size and shape according to the type of medicament contained in said blister.

22. An inhaler for administering dry powder, in combination with a blister pack (B), the inhaler comprising a suction tube (S) having an inlet at one end and an outlet at the other end, the suction tube (S) including at the one end an inlet section (19) configured for successive removal from and insertion into the blister pack (B), the blister pack (B) having a plurality of blisters (8) each containing a dose of powder containing medicament (9), and an inhalation channel (31) providing fluid communication between the inlet and the outlet through which powder is, in use, drawn on inhalation by a user characterised in that the inhaler further comprises a separate support unit (V,G) configured to support the blister pack (B), the support unit (V,G) including a guide wall (6) adjacent which the blister pack (B) is, in use, disposed, the guide wall (6) including a plurality of apertures (15) acting as guide portions in alignment with respective blisters (8) of the blister pack (B), each aperture (15) being for guiding the inlet section (19) of the suction tube (S) into a respective blister (8) of the blister pack (B) and supporting the suction tube (S) when so guided from blister to blister by the user.

23. The inhaler according to claim 22, wherein the support unit (V) is a container within which the blister pack (B) is in use housed.

24. The inhaler according to claim 22, wherein the support unit (V) includes a support member (3) including a plurality of cavities (12) for receiving respective blisters (8) of the blister pack (B), the cavities (12) having the same arrangement as the apertures (15) in the guide wall (6) such that in use the blisters (8) of the blister pack (B) oppose the respective apertures (15).

25. The inhaler according to claim 24, wherein the support member (3) is adapted to be slidable relative to the guide wall (6) so as to allow loading and unloading of blister packs (B).

26. The inhaler according to claim 22, wherein the blister pack (B) includes a substantially planar surface and the support unit (G) includes holding means for holding the substantially planar surface of the blister pack (B) adjacent the guide wall (6).

27. The inhaler according to claim 26, wherein the apertures (15) are defined by elongate sections (36).

28. The inhaler according to claim 27, wherein the length of the elongate sections (36) is greater than the width of the blisters (8) of the blister pack (B).

29. The inhaler according to claim 26, wherein the holding means comprises C-shaped lips for slidably receiving the blister pack (B).

30. The inhaler according to claim 22, wherein the support unit (V,G) includes one or more projections or recesses (41) of predetermined size and position such that the support unit (V,G) can only receive blister packs (B) with corresponding recesses or projections (40).

31. The inhaler according to claim 30, wherein the one or more projections or recesses (41) are sized and positioned such that the support unit (V,G) can only receive blister packs (B) in one relative orientation.

32. The inhaler according to claim 22, wherein the inlet section (19) of the suction tube (S) and each of the apertures (15) are configured such that the inlet section (19) of the suction tube (S) can only be inserted through the apertures (15) in one relative orientation.

33. The inhaler according to claim 32, wherein the cross-section of the inlet section (19) of the suction tube (S) and the cross-section of each of the apertures (15) is rotationally asymmetric.

34. The inhaler according to claim 33, wherein each of the apertures (15) is generally circular in shape with at least one radial extension (16,16',16").

35. The inhaler according to claim 34, wherein a plurality of the apertures (15) are linked by at least one radial extension (16).

36. The inhaler according to claim 22, wherein the support unit (V,G) includes a holder for holding the suction tube (S) when not in use.

37. The inhaler according to claim 36, wherein the holder comprises a chamber (34) with a hinged lid (33).

38. The inhaler according to claim 22, wherein the inlet section (19) of the suction tube (S) includes a cutter (20) having a cutting edge for cutting a covering film (14') of a blister (8) of the blister pack (B).

39. The inhaler according to claim 38, wherein the cutter (20) is located around only a part of the inlet of the suction tube (S) such that upon insertion of the inlet section (19) of the suction tube (S) into a blister (8) of the blister pack (B) the cutter (20) cuts the covering film (14') of the blister (8) such as to leave a single cut film flap.

40. The inhaler according to claim 39, wherein the inlet section includes an outer peripheral surface and an inner peripheral surface the cutting edge of the cutter (20) is disposed at the outer peripheral surface of the inlet section

(19) of the suction tube (S) such that when the inlet section (19) of the suction tube (S) is inserted into a blister (8) of the blister pack (B) the cutter (20) first cuts the covering film (14') of the blister (8) and then the inner peripheral surface of the inlet section (19) of the suction tube (S) pushes the cut film flap into the blister (8).

41. The inhaler according to claim 38, wherein the cutter (20) comprises a plurality of axially extending blades (28), each having cutting edges, separated by axially-extending gaps (26).

42. The inhaler according to claim 22, wherein the inlet section (19) of the suction tube (S) includes at least one passageway (29) for providing fluid communication between a blister (8) of the blister pack (B) and a space above the blister (8) when the inlet section (19) of the suction tube (S) is inserted in the blister (8).

43. The inhaler according to claim 42, wherein the inlet section (19) of the suction tube (S) includes an outer peripheral section and the at least one passageway (29) comprises an open channel in the outer peripheral surface of the inlet section (19) of the suction tube (S), the at least one passageway (29) having one end located at a position along the length of the inlet section (19) of the suction tube (S) and the other end located adjacent the inlet of the suction tube (S).

44. The inhaler according to claim 43, wherein the other end of the at least one passageway (29) is located adjacent the cutter (20).

45. The inhaler according to claim 43, wherein the other end of at least one passageway (29) is located at one of the gaps (26).

46. The inhaler according to claim 43, wherein the other end of the at least one passageway (29) is located between adjacent gaps (26).

47. The inhaler according to claim 42, wherein the at least one passageway (29) comprises a conduit in the inlet section (19) of the suction tube (S), the at least one passageway (29) having an inlet (29') located at a position along the length of the inlet section (19) of the suction tube (S) and an outlet (29") located adjacent the inlet of the suction tube (S).

48. The inhaler according to claim 47, wherein the outlet (29") of the at least one passageway (29) is located adjacent the cutter (20).

49. The inhaler according to claim 47, wherein the outlet (29") of the at least one passageway (29) is located at one of the gaps (26).

50. The inhaler according to claim 47, wherein the outlet (29") of the at least one passageway (29) is located between adjacent gaps (26).

51. The inhaler according to claim 22, wherein the suction tube (S) includes at least one passageway (32) providing fluid communication between the inhalation channel (31) and the atmosphere through which supplementary air is in use drawn into the inhalation channel (31) on inhalation by the user.

52. The inhaler according to claim 22, wherein the inlet section (19) of the suction tube (S) includes a distal end and a radially-extending member defining a shoulder (22) at a predetermined axial distance from the distal end thereof, the shoulder (22) being configured so as in use to abut the blister pack (B) and prevent the inlet section (19) of the suction tube (S) from being inserted too far into a blister (8) of the blister pack (B).

53. The inhaler according to claim 22, further comprising a member connecting the suction tube (S) to the support unit (V,G) from being separated from one another.

* * * * *